(12) United States Patent
Reid

(10) Patent No.: US 11,690,554 B1
(45) Date of Patent: Jul. 4, 2023

(54) EKG CORD MANAGEMENT SYSTEM

(71) Applicant: Donald Reid, Smithtown, NY (US)

(72) Inventor: Donald Reid, Smithtown, NY (US)

( * ) Notice: Subject to any disclaimer, the term of this patent is extended or adjusted under 35 U.S.C. 154(b) by 301 days.

(21) Appl. No.: 16/890,025

(22) Filed: Jun. 2, 2020

(51) Int. Cl.
*A61M 60/592* (2021.01)
*A61M 60/178* (2021.01)
*A61B 5/30* (2021.01)
*H02G 3/04* (2006.01)

(52) U.S. Cl.
CPC .............. *A61B 5/303* (2021.01); *H02G 3/04* (2013.01); *A61B 2562/16* (2013.01); *A61B 2562/222* (2013.01); *A61B 2562/227* (2013.01)

(58) Field of Classification Search
CPC ... A61B 5/282; A61B 2503/045; A61B 5/303; A61B 5/6823
See application file for complete search history.

(56) References Cited

U.S. PATENT DOCUMENTS

| | | | |
|---|---|---|---|
| 5,813,979 A * | 9/1998 | Wolfer | A61B 5/303 600/508 |
| 7,335,053 B2 | 2/2008 | Avevor | |
| 8,369,924 B1 * | 2/2013 | Chang | A61B 5/282 600/509 |
| 9,226,679 B2 | 1/2016 | Balda | |
| D755,726 S | 5/2016 | Michas | |
| 10,130,276 B2 | 11/2018 | Lane | |
| 2008/0265076 A1 | 10/2008 | Petteys | |

FOREIGN PATENT DOCUMENTS

WO    2011146708    11/2011

* cited by examiner

*Primary Examiner* — Jon Eric C Morales

(57) ABSTRACT

The EKG cord management system is a cable management system. The EKG cord management system is configured for use with the leads of an EKG machine. The EKG cord management system comprises a plurality of lead structures, a probe connector, and a housing. The EKG cord management system deploys the plurality of lead structures from the housing. The EKG cord management system retracts the plurality of lead structures into the housing. Each lead structure selected from the plurality of lead structures measures electrical activity in a human body. The probe connector electrically connects each of the plurality of lead structures to a machine known as an EKG machine.

1 Claim, 4 Drawing Sheets

EKG CORD MANAGEMENT SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field Of The Invention

The present invention relates to the field of basic electric elements including electrically conductive connections, more specifically, a means for supporting a coupling part when not engaged. (H01R16/60)

SUMMARY OF INVENTION

The EKG cord management system is a cable management system. The EKG cord management system is configured for use with the leads of an EKG machine. The EKG cord management system comprises a plurality of lead structures, a probe connector, and a housing. The EKG cord management system deploys the plurality of lead structures from the housing. The EKG cord management system retracts the plurality of lead structures into the housing. Each lead structure selected from the plurality of lead structures measures electrical activity in a human body. The probe connector electrically connects each of the plurality of lead structures to a machine known as an EKG machine.

These together with additional objects, features and advantages of the EKG cord management system will be readily apparent to those of ordinary skill in the art upon reading the following detailed description of the presently preferred, but nonetheless illustrative, embodiments when taken in conjunction with the accompanying drawings.

In this respect, before explaining the current embodiments of the EKG cord management system in detail, it is to be understood that the EKG cord management system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the EKG cord management system.

It is therefore important that the claims be regarded as including such equivalent construction insofar as they do not depart from the spirit and scope of the EKG cord management system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
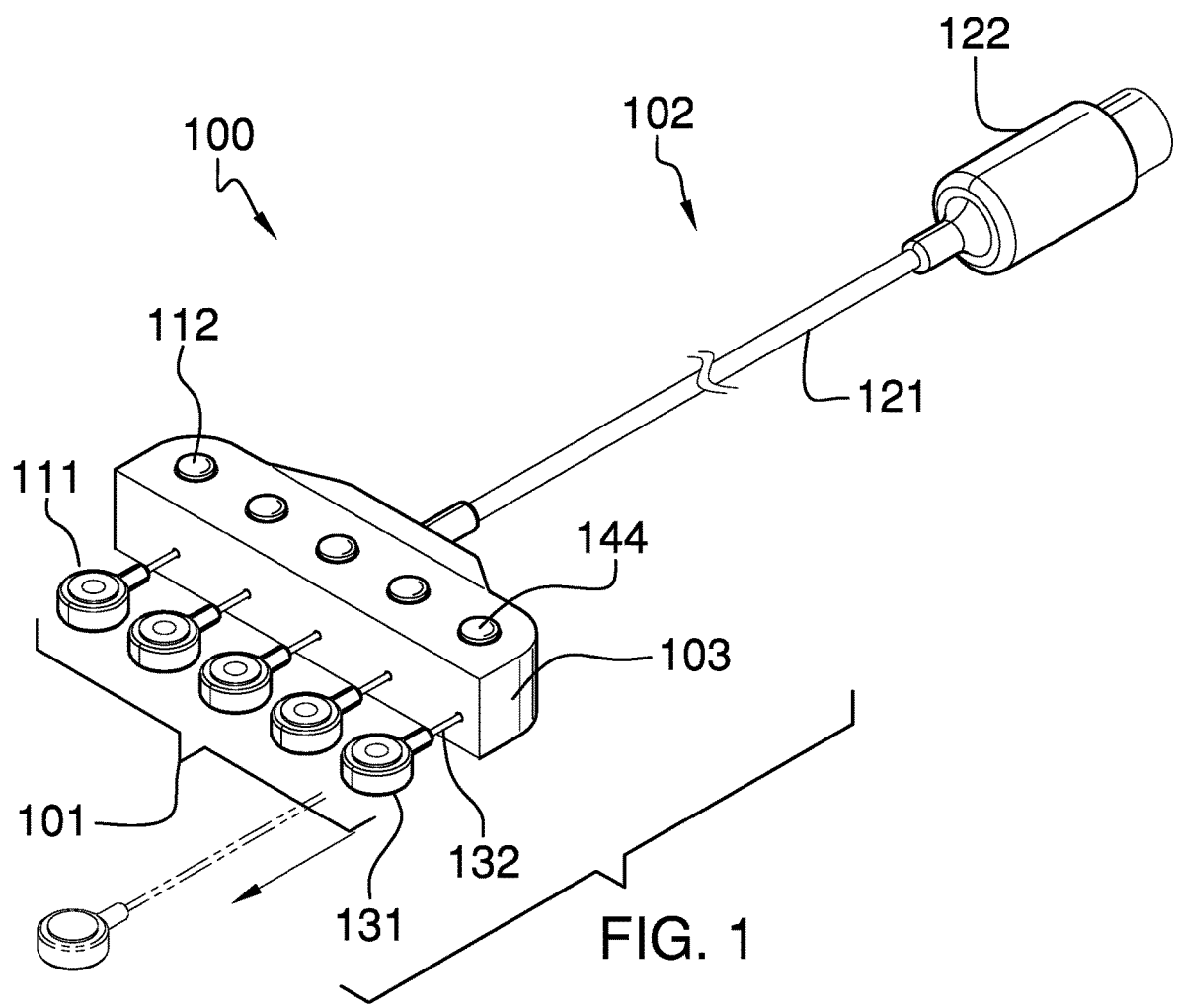
FIG. 1 is a perspective view of an embodiment of the disclosure.
Figure 2:
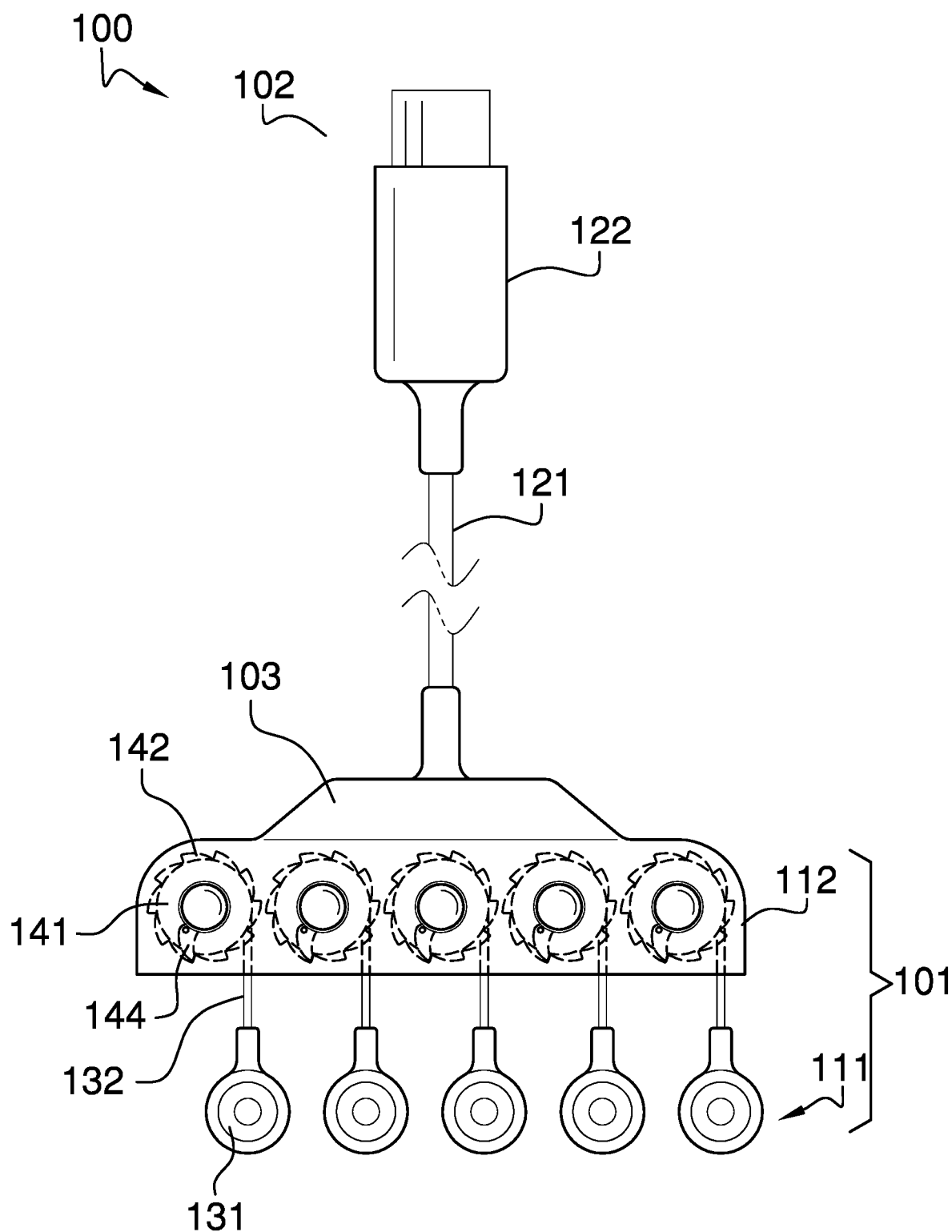
FIG. 2 is a top view of an embodiment of the disclosure.
Figure 3:
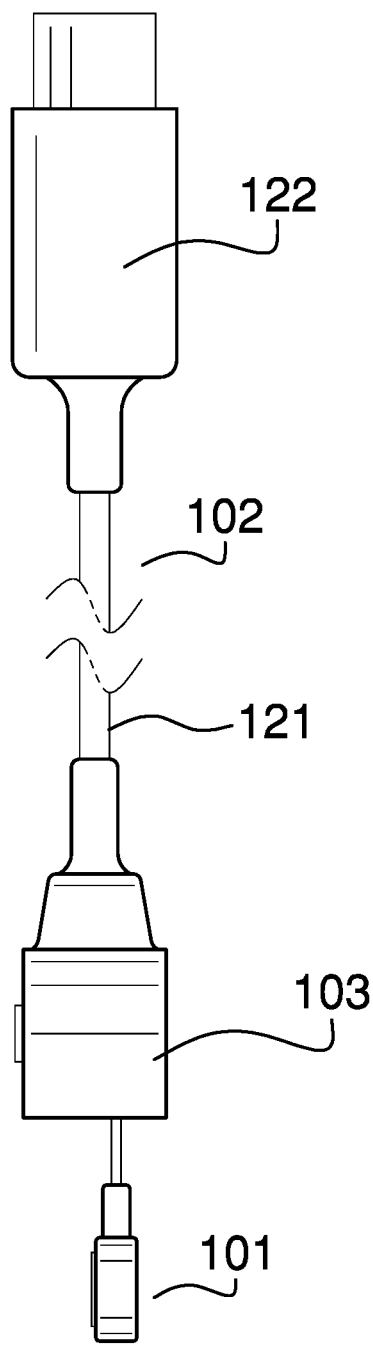
FIG. 3 is a side view of an embodiment of the disclosure.
Figure 4:
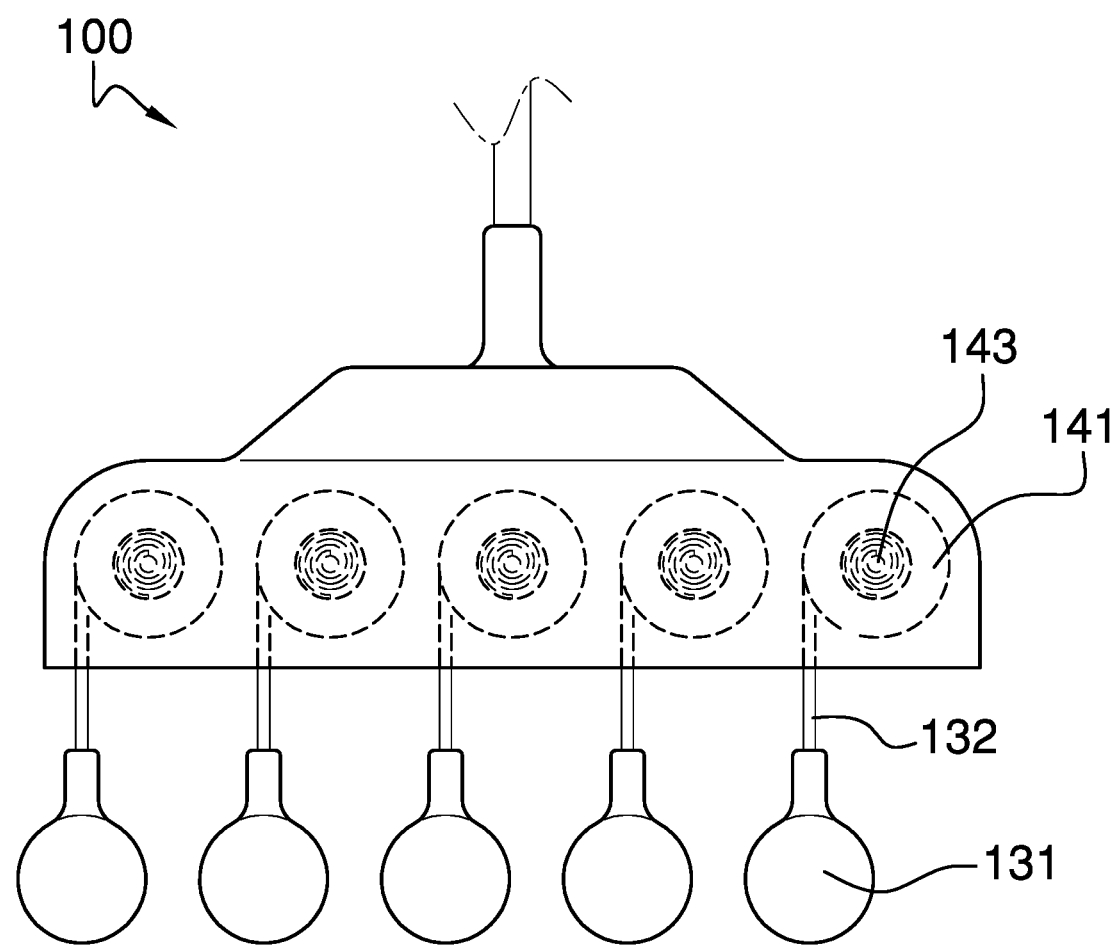
FIG. 4 is a bottom view of an embodiment of the disclosure.

Detailed reference will now be made to one or more potential embodiments of the disclosure, which are illustrated in FIGS. 1 through 4.

The EKG cord management system 100 (hereinafter invention) is a cable management system. The invention 100 is configured for use with the leads for an EKG machine. The invention 100 comprises a plurality of lead structures 101, a probe connector 102, and a housing 103. The invention 100 deploys the plurality of lead structures 101 from the housing 103. The invention 100 retracts the plurality of lead structures 101 into the housing 103 Each lead structure selected from the plurality of lead structures 101 measures electrical activity in a human body. The probe connector 102 electrically connects each of the plurality of lead structures 101 to a machine known as an EKG machine.

The housing 103 is a rigid casing. The housing 103 contains the plurality of lead structures 101. The probe connector 102 attaches to the housing 103. The housing 103 is formed with all apertures and form factors necessary to allow the housing 103 to accommodate the use and operation of the plurality of lead structures 101 and the probe connector 102. Methods to form a housing 103 suitable for the purposes described in this disclosure are well-known and documented in the mechanical arts.

Each of the plurality of lead structures 101 is an electric device. Each of the plurality of lead structures 101 is a sensor. Each of the plurality of lead structures 101 measures the electrical activity generated by the biological processes of a patient. Each of the plurality of lead structures 101 physically attaches to the patient. Each of the plurality of lead structures 101 transmits an electric signal to the probe connector 102. The transmitted electric signal is correlated to the electrical activity measured by the associated individual lead structure. The housing 103 stores each of the plurality of lead structures 101. Each of the plurality of lead structures 101 deploys from the housing 103. Each of the plurality of lead structures 101 retracts into the housing 103.

Each of the plurality of lead structures 101 is independently managed. By independently managed is meant that any first lead structure selected from the plurality of lead structures 101 can be deployed and retracted without impacting the deployment status of any second lead structure selected from the plurality of lead structures 101.

The plurality of lead structures 101 comprises an individual electrode 131 structure 111 and a roller clutch and spring 112.

The individual electrode 131 structure 111 is an electrical device. The individual electrode 131 structure 111 forms a sensor that: a) detects electric activity generated by biological activity in a patient; b) converts the detected electrical activity into an electric signal; and, c) transmits the converted electric signal to the probe connector 102. The individual electrode 131 structure 111 comprises an individual electrode 131 and an individual electrode 131 lead 132.

The individual electrode 131 is an electrode. The electrode is defined elsewhere in this disclosure. The individual electrode 131 is a sensor. The individual electrode 131 attaches to the patient. The individual electrode 131 detects the electrical activity generated by the biological processes of a patient. The individual electrode 131 converts the detected electrical activity into an electric signal. The individual electrode 131 electrically connects to the individual electrode 131 lead 132 such that the converted electric signal is transmitted to the individual electrode 131 lead 132.

The individual electrode 131 lead 132 is an electrically conductive wire. The individual electrode 131 lead 132 is insulated using an insulating material. The individual electrode 131 lead 132 receives the converted electric signal from the individual electrode 131 and physically conducts the transmitted converted electric signal to the probe plug 122 of the probe connector 102.

The roller clutch and spring 112 is a roller clutch and spring 112 system. The roller clutch and spring 112 is defined elsewhere in this disclosure. The roller clutch and spring 112 is a mechanical system. The individual electrode 131 lead 132 of the individual electrode 131 structure 111 spools on the roller clutch and spring 112 such that the individual electrode 131 structure 111 deploys from and retracts onto the roller clutch and spring 112. The roller clutch and spring 112 comprises a spool 141, a spool 141 ratchet 142, a spool 141 spring 143, and a spool 141 clutch 144.

The spool 141 is a prism-shaped structure that stores the individual electrode 131 lead 132 of the roller clutch and spring 112 when the roller clutch and spring 112 is in a retracted position. The spool 141 is defined elsewhere in this disclosure.

The spool 141 ratchet 142 is a ratchet. The ratchet is defined elsewhere in this disclosure. The spool 141 ratchet 142 limits the rotation of the spool 141 such that the spool 141 can only rotate in the deployment direction to deploy the individual electrode 131 lead 132.

The spool 141 clutch 144 is a clutch. The clutch is defined elsewhere in this disclosure. The spool 141 clutch 144 releases the spool 141 ratchet 142 such that the spool 141 will rotate in the retraction direction to retract the individual electrode 131 lead 132.

The spool 141 spring 143 is a spring. The spring is defined elsewhere in this disclosure. The spool 141 spring 143 is deformed as the individual electrode 131 lead 132 is deployed from the spool 141. The spool 141 spring 143 retracts the individual electrode 131 lead 132 onto the spool 141 as the spool 141 spring 143 returns to its relaxed shape after the spool 141 clutch 144 releases the limitation on the rotation of the spool 141 ratchet 142.

The probe connector 102 is an electric device. The probe connector 102 receives the electric signal transmitted by each lead structure selected from the plurality of lead structures 101. The probe connector 102 transmits the received electric signals to a monitoring device such as an EKG machine. The probe connector 102 comprises a probe cable 121 and a probe plug 122.

The probe cable 121 is an electric cable. The probe cable 121 forms an electrical connection between the individual electrode 131 lead 132 of each individual electrode 131 structure 111 selected from the plurality of lead structures 101 and the probe plug 122. The cable is defined elsewhere in this disclosure. The probe cable 121 transmits the converted electric signal to the probe plug 122.

The probe plug 122 is an electric device. The probe plug 122 is a plug. The probe plug 122 forms an electrical connection between the probe cable 121 and the monitoring device such that the monitoring device receives the converted electric signals from the probe cable 121. The plug is defined elsewhere in this disclosure.

The following definitions were used in this disclosure:

Cable: As used in this disclosure, a cable is a collection of one or more insulated wires covered by a protective casing that is used for transmitting electricity or telecommunication signals.

Clutch: As used in this disclosure, a clutch is a mechanical device that attaches and detaches a first rotating device to and from a second device that provides the energy required to rotate the first rotating device.

Cord: As used in this disclosure, a cord is a long, thin, flexible, and prism shaped string, line, rope, or wire. Cords are made from yarns, piles, or strands of material that are braided or twisted together or from a monofilament (such as fishing line). Cords have tensile strength but are too flexible to provide compressive strength and are not suitable for use in pushing objects. String, line, cable, and rope are synonyms for cord.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Electrode: As used in this disclosure, an electrode is an electrical conductor through which electric current enters or exits a non-metallic object that is incorporated into an electric circuit. Non-metallic objects commonly used with electrodes would include, but are not limited to electrolytic solutions, semiconducting materials. The electrode is commonly used on patients undergoing medical procedures.

Form Factor: As used in this disclosure, the term form factor refers to the size and shape of an object.

Housing: As used in this disclosure, a housing is a rigid structure that encloses and protects one or more devices.

Insulating Material: As used in this disclosure, an insulating material is a material that inhibits, and ideally prevents, the transfer of heat through the insulating material. Insulating materials may also be used to inhibit or prevent the transfer of sound or the conduction of electricity through the insulating material. Methods to form insulating materials include, but are not limited to: 1) the use of materials with low thermal conductivity; and, 2) the use of a structural design that places a vacuum within the insulating material within the anticipated transfer path of the heat, sound, or electric current flow.

Lead: As used in this disclosure, a lead is a conductor that is physically used to electrically connect an electrical component into a larger circuit assembly.

Patient: As used in this disclosure, a patient is a person who is designated to receive a medical treatment, therapy or service. The term patient may be extended to an animal when used within the context of the animal receiving veterinary treatment or services.

Plug: As used in this disclosure, a plug is an electrical termination that electrically connects a first electrical circuit to a second electrical circuit or a source of electricity. As used in this disclosure, a plug will have two or three metal pins.

Port: As used in this disclosure, a port is an electrical termination that is used to connect a first electrical circuit to a second external electrical circuit. In this disclosure, the port is designed to receive a plug.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Roller Clutch and Spring System: As used in this disclosure, a roller clutch and spring system is a commercially available system for storing a sheeting on a scroll or loading a cord on a spool. The sheeting is stored on a rotating cylindrical roller as the scroll. The cord is stored on the spool. The clutch portion of the roller clutch and spring system is configured to allow the rotating cylindrical roller to rotate in a first direction. The spring portion of the roller clutch and spring system is configured to return the rotating cylindrical roller to its original position when the clutch portion is released. A common example of the roller clutch and spring system is the mechanism used to raise and lower window blinds.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Spool: As used in this disclosure, a spool is a cylindrical device upon which a flexible material, including but not limited to a yarn, a cord, or a tape, can be wound. Depending on context, a spool may also contain the flexible material stored upon the spool.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An EKG cord management system comprising
a plurality of lead structures, a probe connector, and a housing;
wherein the EKG cord management system deploys the plurality of lead structures from the housing;
wherein the EKG cord management system retracts the plurality of lead structures into the housing each lead structure selected from the plurality of lead structures measures electrical activity in a human body;
wherein the probe connector electrically connects each of the plurality of lead structures to a machine known as an EKG machine;
wherein the EKG cord management system is a cable management system;
wherein the plurality of lead structures comprises an individual electrode structure and a roller clutch and spring;
wherein the individual electrode structure is an electrical device;
wherein the individual electrode structure forms a sensor that: a) detects electric activity generated by biological activity in a patient; b) converts the detected electrical activity into an electric signal; and, c) transmits the converted electric signal to the probe connector;
wherein the roller clutch and spring is a mechanical system;
wherein the individual electrode lead of the individual electrode structure spools on the roller clutch and spring such that the individual electrode structure deploys from and retracts onto the roller clutch and spring;
wherein the roller clutch and spring comprises a spool, a spool ratchet, a spool spring, and a spool clutch;
wherein the spool ratchet limits the rotation of the spool such that the spool can only rotate in the deployment direction to deploy the individual electrode lead;
wherein the spool clutch is a clutch;
wherein the spool clutch releases the spool ratchet such that the spool will rotate in the retraction direction to retract the individual electrode lead;
wherein each of the plurality of lead structures transmits an electric signal to the probe connector;
wherein the transmitted electric signal is correlated to the electrical activity measured by the associated individual lead structure;

wherein the housing stores each of the plurality of lead structures;

wherein each of the plurality of lead structures deploys from the housing;

wherein each of the plurality of lead structures retracts into the housing;

wherein each of the plurality of lead structures is independently managed;

wherein by independently managed is meant that any first lead structure selected from the plurality of lead structures can be deployed and retracted without impacting the deployment status of any second lead structure selected from the plurality of lead structures;

wherein the housing stores each of the plurality of lead structures in a linearly-aligned arrangement such that each of the plurality of lead structures deploys independently of one another from the housing;

wherein the probe connector is an electric device;

wherein the probe connector receives the electric signal transmitted by each lead structure selected from the plurality of lead structures;

wherein the probe connector transmits the received electric signals to a monitoring device such as an EKG machine;

wherein the probe connector comprises a probe cable and a probe plug;

wherein the probe cable forms an electrical connection between the individual electrode lead of each individual electrode structure selected from the plurality of lead structures and the probe plug;

wherein the individual electrode structure comprises an individual electrode and an individual electrode lead;

wherein the individual electrode is an electrode;

wherein the individual electrode converts the detected electrical activity into an electric signal;

wherein the individual electrode electrically connects to the individual electrode lead such that the converted electric signal is transmitted to the individual electrode lead;

wherein the individual electrode lead is an electrically conductive wire;

wherein the individual electrode lead is insulated using an insulating material;

wherein the individual electrode lead receives the converted electric signal from the individual electrode and physically conducts the transmitted converted electric signal to the probe connector;

wherein the housing is a rigid casing;

wherein the housing contains the plurality of lead structures;

wherein the probe connector attaches to the housing;

wherein each of the plurality of lead structures is an electric device;

wherein each of the plurality of lead structures is a sensor;

wherein each of the plurality of lead structures measures the electrical activity generated by the biological processes;

wherein the individual electrode is a sensor;

wherein the individual electrode detects the electrical activity generated by the biological processes;

wherein the spool spring retracts the individual electrode lead onto the spool as the spool spring returns to its relaxed shape after the spool clutch releases the limitation on the rotation of the spool ratchet;

wherein the spool is a prism-shaped structure that stores the individual electrode lead of the roller clutch and spring when the roller clutch and spring is in a retracted position;

wherein the spool ratchet is a ratchet;

wherein the spool spring is a spring;

wherein the spool spring is deformed as the individual electrode lead is deployed from the spool;

wherein the probe cable is an electric cable;

wherein the probe cable transmits the converted electric signal to the probe plug;

wherein the probe plug is an electric device;

wherein the probe plug is a plug;

wherein the probe plug forms an electrical connection between the probe cable and the monitoring device such that the monitoring device receives the converted electric signals from the probe cable.

* * * * *